United States Patent [19]
Verrips et al.

[11] Patent Number: 4,771,000
[45] Date of Patent: Sep. 13, 1988

[54] STRUCTURAL GENES ENCODING THE VARIOUS ALLELIC AND MATURATION FORMS OF PREPROTHAUMATIN, RECOMBINANT CLONING VEHICLES COMPRISING SAID STRUCTURAL GENES AND EXPRESSION THEREOF IN TRANSFORMED MICROBIAL HOST CELLS

[75] Inventors: Cornelis T. Verrips, Maassluis; Jan Maat, Monster; Luppo Edens, Maassluis; Adrianus M. Ledeboer, Rotterdam, all of Netherlands

[73] Assignee: Internationale Octrooi Maatschappij Octropa B.V., Rotterdam, Netherlands

[21] Appl. No.: 732,818

[22] Filed: May 10, 1985

Related U.S. Application Data

[63] Continuation of Ser. No. 329,830, Dec. 11, 1981, abandoned.

[30] Foreign Application Priority Data

Dec. 12, 1980 [GB] United Kingdom ................ 8039854

[51] Int. Cl.$^4$ ....................... C12P 21/02; C12P 21/00; C12P 21/04; C12P 19/34; C12N 15/00; C12N 1/20; C07H 21/04
[52] U.S. Cl. ......................................... 435/70; 435/68; 435/71; 435/91; 435/172.1; 435/172.3; 435/253; 435/320; 536/27; 935/11; 935/29; 935/38; 935/60; 935/73
[58] Field of Search .................. 435/68, 70, 91, 172.3, 435/253, 317, 11, 29, 38, 72–75, 60; 536/27

[56] References Cited

U.S. PATENT DOCUMENTS 4,237,224 12/1980 Cohen .................................... 435/68
4,321,365 3/1982 Wu et al. ............................... 435/91
4,336,336 6/1982 Silhavy et al. ......................... 435/68

FOREIGN PATENT DOCUMENTS 1565190 5/1978 United Kingdom ............. 435/172.3

OTHER PUBLICATIONS

Roberts et al., "A General Method for Maximizing the Expression of a Cloned Gene", Proc, Natl. Acad. Sci. U.S.A. 76: 760 (1979).
Iyengar et al.: Chem. Abstr. 91, 118895c (1979).
Helling et al.: in *Genetic Engineering* (Chakrabarty (ed.), CRC Press, 1978, pp. 1–30.
Messing: Recombinant DNA Technical Bulletin, vol. 2, pp. 43–48 (1979).
Stauffer et al.: Proc. Natl. Acad. Sci. U.S.A. 75, 4833 (1978).
Nature, vol. 284, No. 5758, Apr. 24, 1980, p. 653.
Nature, vol. 281, Oct. 18, 1979, pp. 544–548, Goéddel et al.
Eur. J. Biochem., 1979, 96(1), 193–204, Ivengar et al.
G. Blobel et al., (1975), J. Cell. Biol. 67, 835–851.
D. Koshland et al., (1980), Cell 20, 749–760.
F. Lee et al., J. Mol. Biol. 121, 193–217, (1978).
K. Bertrand et al., Science 189, 22–26, (1975).
P. M. G. F. VanWezenbeek et al., Gene 11, 129–148, (1980).
K. S. Kirby, (1965), Biochem. J. 96, 226–269.
U. Wiegers et al., (1972), FEBS Letters 23, 77–82.
H. Avir et al., (1972), Proc. Natl. Acad. Sci., U.S.A., 69, 1408–1412.
J. W. Davies et al., (1973), J. Virol. 12, 1434–1441.
G. N. Buell et al., J. Biol. Chem., (1978), 253, 2471–2482.

(List continued on next page.)

Primary Examiner—James Martinell
Attorney, Agent, or Firm—Cushman, Darby & Cushman

[57] ABSTRACT

The invention relates to structural genes comprising encoding non-processed and partly processed thaumatin, to the various allelic forms of said non-processed thaumatin and to recombinant DNA's and plasmids comprising said structural genes coding for the various allelic forms of preprothaumatin, and naturally and/or artifically modified preprothaumatin in various stages of its natural processing, and to the use of said recombinant plasmids to transform microorganisms, particularly bacteria in which said genes are expressed.

6 Claims, 21 Drawing Sheets

OTHER PUBLICATIONS

A. R. Davies et al., Gene 10, 205–218, (1980).

R. Roychoudhury et al., (1976), Nucleic Acids Research 3, 863–877.

H. C. Birnboim et al., Nucleic Acids Research 7, 1513–1523, (1979).

J. G. Williams et al., Cell 17, 903–913, (1979).

A. M. Maxam et al., Methods in Enzymology, L. Grossmann et al., editors, N.Y. Acad. Press, 1980, vol. 65(1), pp. 499–560.

J. Maat et al., Nucleic Acids Research 5, 4537–4545, (1978).

D. Zimmern et al., Proc. Natl. Acad. Sci., U.S.A. 75, 4257–4261, (1978).

K. Backman et al., Cell 13, 65–71, (1978).

R. A. Hallewell et al., Gene 9, 27–47, (1980).

J. F. M. de Rooy et al., Recl. Trav. Chim., Pays Bas, 98, 537–548, (1979).

Edens et al.; Gene. 18 (1982), 1–12 Elsevier Biomedical Press; Cloning of cDNA Encoding the Sweet-Tasting Plant Protein Thaumatin and Its Expression in *Escherichia Coli*.

van der Wel et al.: Eur. J. Biochem. 31, 221 (1972).

Fig. 1.

Amino acid and nucleotide sequence corresponding to one of the allelic forms of the preprothaumatine protein molecule and mRNA/DNA molecule

```
1                                          MET ALA ALA THR THR CYS PHE PHE PHE LEU
AAAG CGC AGC CTC AAT TGG CAT CAT ACA TCA ATG CCC GCC ACC ACT TGC TTC TTC TTC CTC

62
PHE PRO PHE LEU LEU LEU LEU THR LEU SER ARG ALA ALA THR PHE GLU ILE VAL ASN ARG
TTC CCC TTC CTC CTC CTC CTC ACG CTC TCC CGC GCT GCC ACC TTC GAG ATC GTC AAC CGC

122
CYS SER TYR THR VAL TRP ALA ALA ALA SER LYS GLY ASP ALA ALA LEU ASP ALA GLY GLY
TGC TCC TAC ACC GTG TGG GCG GCC GCC TCC AAA GGC GAC GCC GCC CTG GAC GCC GGC GGC

182
ARG GLN LEU ASN SER GLY GLU SER TRP THR ILE ASN VAL GLU PRO GLY THR LYS GLY GLY
CGC CAG CTC AAC TCG GGA GAG TCC TGG ACC ATC AAC GTA GAA CCC GGC ACC AAG GGT GGC

242
LYS ILE TRP ALA ARG THR ASP CYS TYR PHE ASP ASP SER GLY ARG GLY ILE CYS ARG THR
AAA ATC TGG GCC CGC ACC GAC TGC TAT TTC GAC GAC AGC GGC CGC GGC ATC TGC CGG ACC

302
GLY ASP CYS GLY GLY LEU LEU GLN CYS LYS ARG PHE GLY ARG PRO PRO THR THR LEU ALA
GGC GAC TGC GGC GGC CTC CTC CAG TGC AAG CGC TTC GGC CGG CCG CCC ACC ACG CTG GCC

362
GLU PHE SER LEU ASN GLN TYR GLY LYS ASP TYR ILE ASP ILE SER ASN ILE LYS GLY PHE
GAG TTC TCG CTC AAC CAG TAC GGC AAG GAC TAC ATC GAC ATC TCC AAC ATC AAA GGC TTC

422
ASN VAL PRO MET ASP PHE SER PRO THR THR ARG GLY CYS ARG GLY VAL ARG CYS ALA ALA
AAC GTG CCG ATG GAC TTC AGC CCG ACC ACG CGC GGC TGC CGC GGG GTG CGC TGC GCC GCC

482
ASP ILE VAL GLY GLN CYS PRO ALA LYS LEU LYS ALA PRO GLY GLY GLY CYS ASN ASP ALA
GAC ATC GTG GGG CAG TGC CCC GCG AAG CTG AAG GCG CCG GGG GGT GGT TGC AAC GAT GCG

542
CYS THR VAL PHE GLN THR SER GLU TYR CYS CYS THR THR GLY LYS CYS GLY PRO THR GLU
TGC ACC GTG TTC CAG ACG AGC GAG TAC TGC TGC ACC ACG GGG AAG TGC GGG CCG ACG GAG

602
TYR SER ARG PHE PHE LYS ARG LEU CYS PRO ASP ALA PHE SER TYR VAL LEU ASP LYS PRO
TAC TCC CGC TTC TTC AAG AGG CTT TGC CCG GAC GCG TTC AGT TAT GTC CTG GAC AAG CCA

662
THR THR VAL THR CYS PRO GLY SER SER ASN TYR ARG VAL THR PHE CYS PRO THR ALA LEU
ACC ACC GTC ACC TGC CCC GGC AGC TCC AAC TAC AGG GTC ACT TTC TGC CCT ACT GCC CTT

722
GLU LEU GLU ASP GLU
GAA CTT GAA GAC GAC TAA GAG GAT GAA GAC GGA CAC TGA GGA TAC GCA ATA AAA GAA TAA

782
GAT GAT AAG CAA TTA TAT CAA TAA AAA GGG TAC GTG GTT TAC GTC GAG AAG GCA TCA GCT

842
TGG GAG GAA AAG TGT TAT AAA ATA TGT GTG TGG GGA TTG GCT AAT TAA ACT TGT AAA ATA

902
TAA ATA AAA GTT CTC CGT TTT GAC GTG TGC AAA AAA AAA AAA AAA AAA AAA AAA AAA AAA
```

Fig. 2.

Amino acid and nucleotide sequence corresponding to preprothaumatin and the coding strand of its structural gene

```
  32
  MET ALA ALA THR THR CYS PHE PHE PHE LEU PHE PRO PHE LEU LEU LEU LEU THR LEU SER
  ATG GCC GCC ACC ACT TGC TTC TTC TTC CTC TTC CCC TTC CTC CTC CTC CTC ACG CTC TCC

92
  ARG ALA ALA THR PHE GLU ILE VAL ASN ARG CYS SER TYR THR VAL TRP ALA ALA ALA SER
  CGC GCT GCC ACC TTC GAG ATC GTC AAC CGC TGC TCC TAC ACC GTG TGG GCG GCC GCC TCC

152
  LYS GLY ASP ALA ALA LEU ASP ALA GLY GLY ARG GLN LEU ASN SER GLY GLU SER TRP THR
  AAA GGC GAC GCC GCC CTG GAC GCC GGC GGC CGC CAG CTC AAC TCG GGA GAG TCC TGG ACC

212
  ILE ASN VAL GLU PRO GLY THR LYS GLY GLY LYS ILE TRP ALA ARG THR ASP CYS TYR PHE
  ATC AAC GTA GAA CCC GGC ACC AAG GGT GGC AAA ATC TGG GCC CGC ACC GAC TGC TAT TTC

272
  ASP ASP SER GLY ARG GLY ILE CYS ARG THR GLY ASP CYS GLY GLY LEU LEU GLN CYS LYS
  GAC GAC AGC GGC CGC GGC ATC TGC CGG ACC GGC GAC TGC GGC GGC CTC CTC CAG TGC AAG

332
  ARG PHE GLY ARG PRO PRO THR THR LEU ALA GLU PHE SER LEU ASN GLN TYR GLY LYS ASP
  CGC TTC GGC CGG CCG CCC ACC ACG CTG GCG GAG TTC TCG CTC AAC CAG TAC GGC AAG GAC

392
  TYR ILE ASP ILE SER ASN ILE LYS GLY PHE ASN VAL PRO MET ASP PHE SER PRO THR THR
  TAC ATC GAC ATC TCC AAC ATC AAA GGC TTC AAC GTC CCG ATG GAC TTC AGC CCC ACC ACG

452
  ARG GLY CYS ARG GLY VAL ARG CYS ALA ALA ASP ILE VAL GLY GLN CYS PRO ALA LYS LEU
  CGC GGC TGC CGC GGG GTG CGG TGC GCC GCC GAC ATC GTG GGG CAG TGC CCG GCG AAG CTG

512
  LYS ALA PRO GLY GLY GLY CYS ASN ASP ALA CYS THR VAL PHE GLN THR SER GLU TYR CYS
  AAG GCG CCG GGG GGT GGT TGC AAC GAT GCG TGC ACC GTG TTC CAG ACG AGC GAG TAC TGC

572
  CYS THR THR GLY LYS CYS GLY PRO THR GLU TYR SER ARG PHE PHE LYS ARG LEU CYS PRO
  TGC ACC ACG GGG AAG TGC GGG CCG ACG GAG TAC TCG CGC TTC TTC AAG AGG CTT TGC CCC

632
  ASP ALA PHE SER TYR VAL LEU ASP LYS PRO THR THR VAL THR CYS PRO GLY SER SER ASN
  GAC GCG TTC AGT TAT GTC CTG GAC AAG CCA ACC ACC GTC ACC TGC CCC GGC AGC TCC AAC

692
  TYR ARG VAL THR PHE CYS PRO THR ALA LEU GLU LEU GLU ASP GLU
  TAC AGG GTC ACT TTC TGC CCT ACT GCC CTT GAA CTT GAA GAC GAG
```

Fig. 3.

Amino acid and DNA sequence corresponding to prothaumatin and the coding strand of its structural gene

```
 98
ALA THR PHE GLU ILE VAL ASN ARG CYS SER TYR THR VAL TRP ALA ALA ALA SER LYS GLY
GCC ACC TTC GAG ATC GTC AAC CGC TGC TCC TAC ACC GTG TGG GCG GCC GCC TCC AAA GGC

158
ASP ALA ALA LEU ASP ALA GLY GLY ARG GLN LEU ASN SER GLY GLU SER TRP THR ILE ASN
GAC GCC GCC CTG GAC GCC GGC GGC CGC CAG CTC AAC TCG GGA GAG TCC TGG ACC ATC AAC

218
VAL GLU PRO GLY THR LYS GLY GLY LYS ILE TRP ALA ARG THR ASP CYS TYR PHE ASP ASP
GTA GAA CCC GGC ACC AAG GGT GGC AAA ATC TGC GCC CGC ACC GAC TGC TAT TTC GAC GAC

278
SER GLY ARG GLY ILE CYS ARG THR GLY ASP CYS GLY GLY LEU LEU GLN CYS LYS ARG PHE
AGC GGC CGC GGC ATC TGC CGG ACC GGC GAC TGC GGC GGC CTC CTC CAG TGC AAG CGC TTC

338
GLY ARG PRO PRO THR THR LEU ALA GLU PHE SER LEU ASN GLN TYR GLY LYS ASP TYR ILE
GGC CGG CCG CCC ACC ACG CTG GCG GAG TTC TCG CTC AAC CAG TAC GGC AAG GAC TAC ATC

398
ASP ILE SER ASN ILE LYS GLY PHE ASN VAL PRO MET ASP PHE SER PRO THR THR ARG GLY
GAC ATC TCC AAC ATC AAA GGC TTC AAC GTG CCG ATG GAC TTC AGC CCG ACC ACG CGC GGC

458
CYS ARG GLY VAL ARG CYS ALA ALA ASP ILE VAL GLY GLN CYS PRO ALA LYS LEU LYS ALA
TGC CGC GGG GTG CGG TGC GCC GCC GAC ATC GTG GGG CAG TGC CCG GCG AAG CTG AAG GCG

518
PRO GLY GLY GLY CYS ASN ASP ALA CYS THR VAL PHE GLN THR SER GLU TYR CYS CYS THR
CCG GGG GGT GGT TGC AAC GAT GCG TGC ACC GTG TTC CAG ACC AGC GAG TAC TGC TGC ACC

578
THR GLY LYS CYS GLY PRO THR GLU TYR SER ARG PHE PHE LYS ARG LEU CYS PRO ASP ALA
ACG GGC AAG TGC GGG CCG ACG GAG TAC TCG CGC TTC TTC AAG AGG CTT TGC CCG GAC GCC

638
PHE SER TYR VAL LEU ASP LYS PRO THR THR VAL THR CYS PRO GLY SER SER ASN TYR ARG
TTC AGT TAT GTC CTG GAC AAG CCA ACC ACC GTC ACC TGC CCC GGC AGC TCC AAC TAC AGG

698
VAL THR PHE CYS PRO THR ALA LEU GLU LEU GLU ASP GLU
GTC ACT TTC TGC CCT ACT GCC CTT GAA CTT GAA GAC GAG
```

Fig.4.

Amino acid and DNA sequence corresponding to prethaumatin and the coding strand of its structural gene

```
32
MET ALA ALA THR THR CYS PHE PHE PHE LEU PHE PRO PHE LEU LEU LEU LEU THR LEU SER
ATG GCC GCC ACC ACT TGC TTC TTC TTC CTC TTC CCC TTC CTC CTC CTC CTC ACG CTC TCC

92
ARG ALA ALA THR PHE GLU ILE VAL ASN ARG CYS SER TYR THR VAL TRP ALA ALA ALA SER
CGC GCT GCC ACC TTC GAG ATC GTC AAC CGC TGC TCC TAC ACC GTG TGG GCG GCC GCC TCC

152
LYS GLY ASP ALA ALA LEU ASP ALA GLY GLY ARG GLN LEU ASN SER GLY GLU SER TRP THR
AAA GGC GAC GCC GCC CTG GAC GCC GGC GGC CGC CAG CTC AAC TCG GGA GAG TCC TGG ACC

212
ILE ASN VAL GLU PRO GLY THR LYS GLY GLY LYS ILE TRP ALA ARG THR ASP CYS TYR PHE
ATC AAC GTA GAA CCC GGC ACC AAG GGT GGC AAA ATC TGG GCC CGC ACC GAC TGC TAT TTC

272
ASP SER GLY ARG GLY ILE CYS ARG THR GLY ASP CYS GLY GLY LEU LEU GLN CYS LYS
GAC GAC AGC GGC CGC GGC ATC TGC CGG ACC GGC GAC TGC GGC GGC CTC CTC CAG TGC AAG

332
ARG PHE GLY ARG PRO PRO THR THR LEU ALA GLU PHE SER LEU ASN GLN TYR GLY LYS ASP
CGC TTC GGC CGG CCG CCC ACC ACG CTG GCG GAG TTC TCG CTC AAC CAG TAC GGC AAG GAC

392
TYR ILE ASP ILE SER ASN ILE LYS GLY PHE ASN VAL PRO MET ASP PHE SER PRO THR THR
TAC ATC GAC ATC TCC AAC ATC AAA GGC TTC AAC GTG CCG ATG GAC TTC AGC CCG ACC ACG

452
ARG GLY CYS ARG GLY VAL ARG CYS ALA ALA ASP ILE VAL GLY GLN CYS PRO ALA LYS LEU
CGC GGC TGC CGC GGG GTG CGG TGC GCC GCC GAC ATC GTG GGG CAG TGC CCG GCG AAG CTG

512
LYS ALA PRO GLY GLY GLY CYS ASN ASP ALA CYS THR VAL PHE GLN THR SER GLU TYR CYS
AAG GCG CCG GGG GGT GGT TGC AAC GAT GCG TGC ACC GTG TTC CAG ACG AGC GAG TAC TGC

572
CYS THR THR GLY LYS CYS GLY PRO THR GLU TYR SER ARG PHE PHE LYS ARG LEU CYS PRO
TGC ACC ACG GGG AAG TGC GGG CCG ACG GAG TAC TCG CGC TTC TTC AAG AGG CTT TGC CCG

632
ASP ALA PHE SER TYR VAL LEU ASP LYS PRO THR THR VAL THR CYS PRO GLY SER SER ASN
GAC GCC TTC AGT TAT GTC CTG GAC AAG CCA ACC ACC GTC ACC TGC CCC GGC AGC TCC AAC

692
TYR ARG VAL THR PHE CYS PRO THR ALA
TAC AGG GTC ACT TTC TGC CCT ACT GCC
```

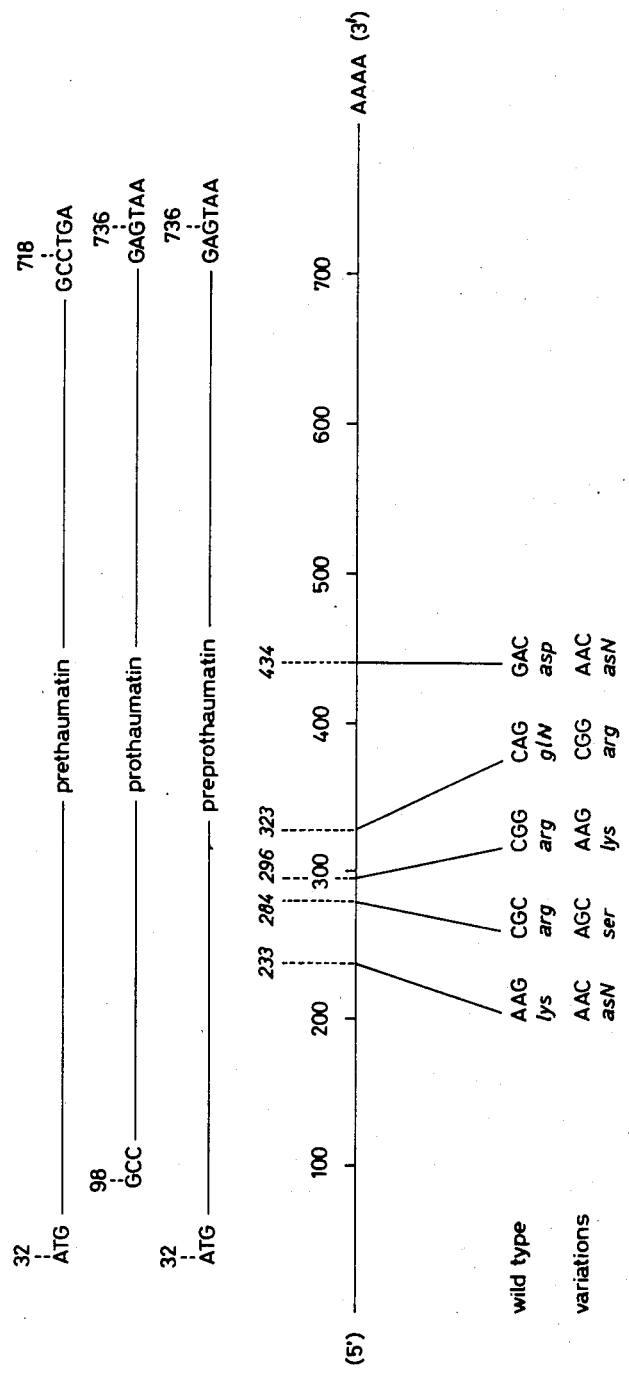
Fig. 5 Allelic variations in the preprothaumatin gene.

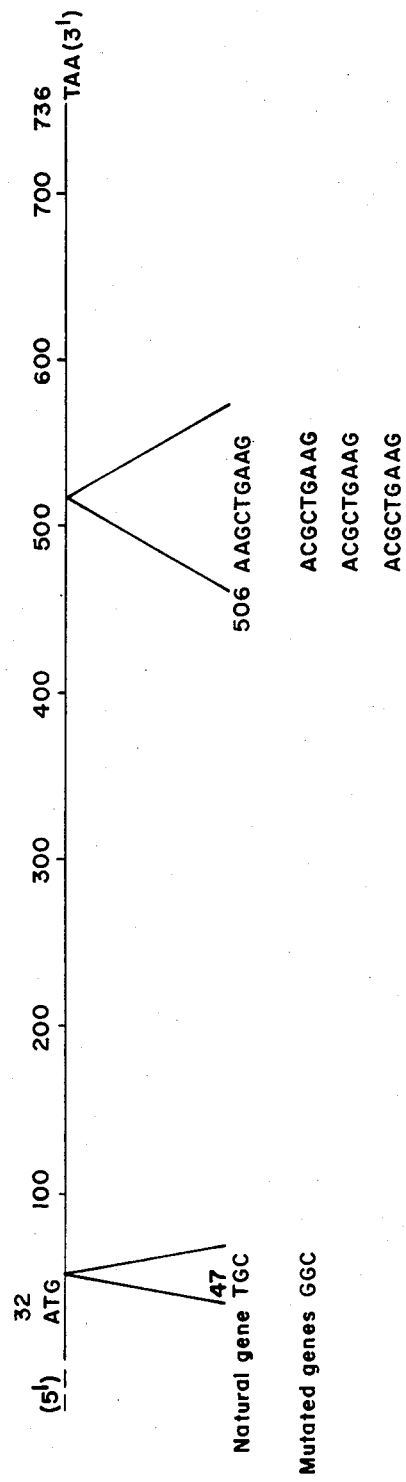
Fig. 6. SOME OF THE MUTATIONS INTRODUCED IN THE VARIOUS ALLELIC GENES ENCODING PREPROTHAUMATIN
NOTE: The above-mentioned variations are present in all possible variations.

Fig. 10. Construction of the preprothaumatin gene without G/C-tails.

Fig. 11 Construction of pUR 101.

Fig. 12 Construction of single stranded M13-DNA templates M13-101-A and M13-101-B.

Fig. 13 Construction of pUR 102 (encoding prethaumatin).

Fig. 14 Construction of pUR 103 (encoding prothaumatin).

Fig. 15 Construction of M13-Tha 47 containing preprothaumatin encoding sequences with a mutation at position 47 (cf fig. 1).

Fig. 16 Construction of M13-phages Tha 507, 513 and 507/513 with special mutations at 507 and/or 513.

Fig. 17 Construction of pUR 521, 531 and 541 with preprothaumatin encoding DNA sequences under transcriptional control.

Fig. 18 Construction of pUR 522, 532, 542 with prethaumatin encoding DNA sequences under transcriptional control.

Fig. 19 Construction of pUR 523, 533, 543 with prothaumatin encoding DNA sequences under transcriptional control.

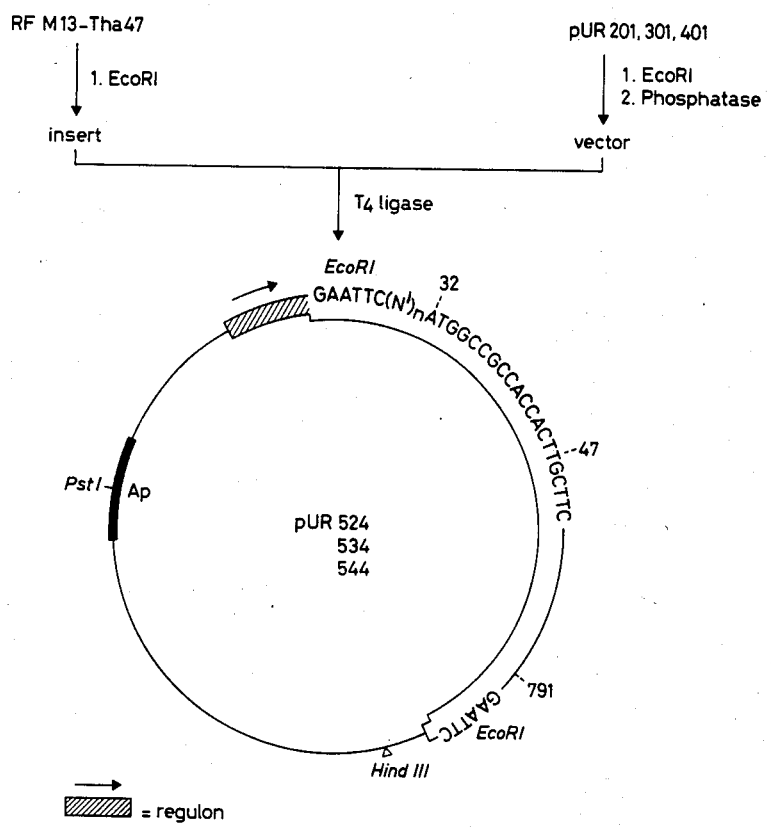
Fig. 20 Construction of pUR 524, 534 and 544 with a mutated preprothaumatin DNA sequence under trancriptional control.

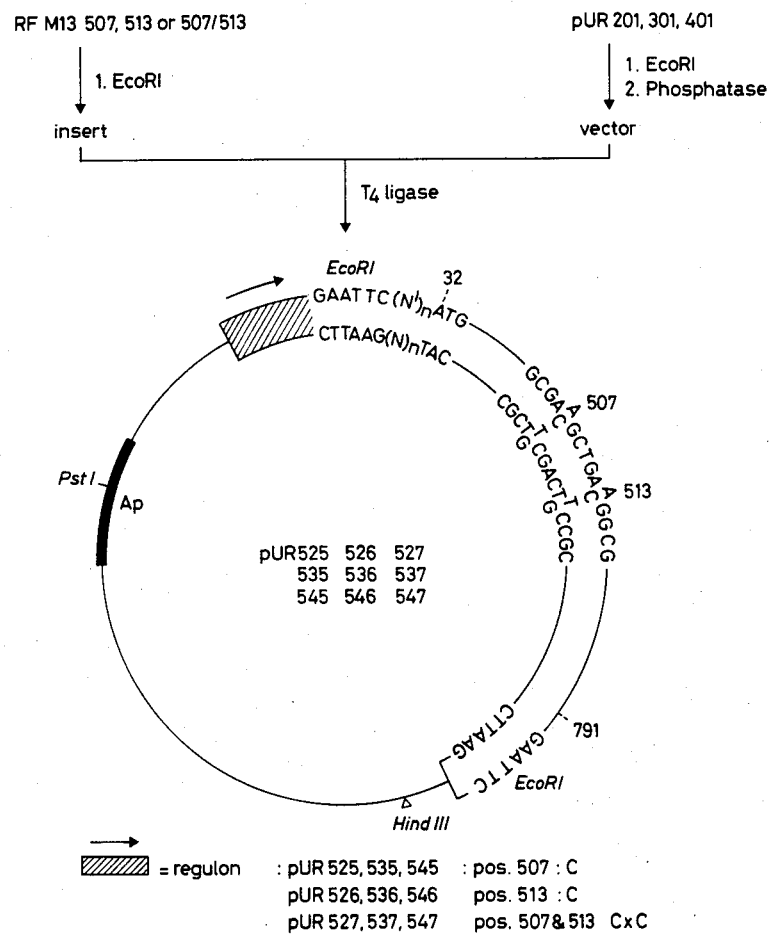
Fig. 21 Construction of pUR 525, 535, 545, 526, 536, 546, 527, 537, 547 with mutated preprothaumatin encoding DNA sequences under transcriptional control.

STRUCTURAL GENES ENCODING THE VARIOUS ALLELIC AND MATURATION FORMS OF PREPROTHAUMATIN, RECOMBINANT CLONING VEHICLES COMPRISING SAID STRUCTURAL GENES AND EXPRESSION THEREOF IN TRANSFORMED MICROBIAL HOST CELLS

This is a continuation of application Ser. No. 329,830, filed Dec. 11, 1981, which was abandoned upon the filing hereof.

The present invention relates to structural genes consising encoding non-processed and partly processed thaumatin, to the various allelic forms of said non-processed thaumatin and to recombinant DNA's and plasmids comprising said structural genes coding for the various allelic forms of preprothaumatin, and naturally and/or artificially modified preprothaumatin in various stages of its natural processing, and to the use of said recombinant plasmids to transform microorganisms, particularly bacteria in which said genes are expressed.

Thaumatin is a protein originating from the arils of the fruit of *Thaumatococcus daniellii*. Thaumatin is, on a weight basis, 1600 times sweeter than sucrose and on a molecular basis $10^5$ times sweeter than sucrose. In Western society overconsumption of sugar causes a number of health problems. Therefore, many attempts have been made to substitute low caloric sweeteners for sugar. However, several of these have recently been prohibited in view of possible side-effects. There is thus a need for a natural low caloric sweetener and for an economical process of producing such a sweetener. Recent advances in molecular biology have enabled the introduction of genes coding for specific eukaryotic proteins into microbial host cells and expressing said genes in the transformed host cells, thereby producing the desired protein.

Many genes of eukaryotic origin which in their natural state encode proteins in their unprocessed forms, can not be applied directly in recombinant DNA molecules because natural genes contain DNA sequences called introns, which are not contained in the messenger RNA (mRNA). The information located on these introns is removed in eukaryotic cells before the translation process of the mRNA. As far as Applicants are aware, bacteria are unable to excise such introns at the RNA level and therefore it is necessary to remove the genetic information located on these introns at DNA level before the natural gene of eukaryotes can be used in prokaryotic host cells.

In microbial host cells, that have the capability of excising introns at mRNA level, the natural genes can in principle be applied, provided that they are brought under control of regulons that are effective in said microbial host cells.

For economic reasons it is important that proteins encoded by the recombinant DNA gene are produced under optimal conditions. The main routes to achieve this are:

(1) integration of the structural gene down-stream of an effective regulon, in such a way that under selected growth conditions, the amount of protein produced per cell (by an optimal number of cells) is as high as possible.

For that purpose regulons like the double lac UV5 and the trp regulon of *E. coli* and the regulon of the gene VIII product of the bacteriophages M13, fd and f1 are, amongst others, adequate in their natural state or in their processed form(s).

(2) excretion of said protein by microbial host cells into their periplasmic space and/or into the culturing medium, thus preventing said protein from intracellular degradation or preventing the disturbance of the normal cellular processes due to too high an intracellular level of said protein. It is now generally accepted that in many prokaryotic- and eukaryotic cells a special $NH_2$-terminal amino acid sequence of the unprocessed form of the proteins is involved in the protein excretion process. G. Blobel and B. Dobberstein (1975), J. Cell Biol. 67, 835–851.

Recently it was proved that also the COOH-terminal amino acid sequence of the protein can also play a role in this process. D. Koshland and D. Botstein (1980), Cell 20, 749–760.

Therefore it would be of high economic importance if proteins encoded by recombinant DNA molecules had at their $NH_2$— and/or COOH— terminus amino acid sequences that promote the excretion of said proteins by microbial cells.

In the present invention use is made of recombinant DNA and other molecular biological techniques to construct recombinant DNA molecules that fulfil the above-described requirements.

The present invention is also related to the change of the genetic information of structural genes using site-directed mutagenesis.

For a better understanding of the invention the most important terms used in the description will be defined:

A regulon is a DNA sequence consisting of a promotor and operator region.

Structural genes are DNA sequences which encode through a template (mRNA) a sequence of amino acids characteristic of a specific polypeptide.

A promoter is a DNA sequence within the regulon to which RNA polymerase binds for the initiation of the transcription.

An operator is a DNA sequence within the regulon to which a repressor protein may bind, thus preventing RNA polymerase from binding to the adjacent promoter.

An inducer is a substance which deactivates a repressor protein, freeing the operator and permitting RNA polymerase to bind to the promoter and start transcription.

By preprothaumatin is meant one of the allelic forms of the unprocessed protein (FIG. 4).

Cloning vehicle. A non-chromosomal double-stranded DNA, plasmid or phage, comprising a DNA sequence (intact replicon) that allows self-replication after transformation into suitable host cells.

Phage or bacteriophage. Bacterial virus which can replicate in a suitable bacterial host cell.

Reading frame. The grouping of triplets of nucleotides (codons) into such a frame that at mRNA level a proper translation of the codons into the polypeptide takes place.

Transcription. The process of producing RNA from a gene.

Translation. The process of producing a polypeptide from mRNA.

Expression. The process undergone by a structural gene to produce a polypeptide. It is a combination of many processes, including at least transcription and translation.

By preprothaumatin gene is meant the double-stranded DNA sequence having exactly the same information (sequence of codons) as that part of the messenger RNA coding for unprocessed preprothaumatin.

By signal peptide is meant that part of the preproprotein which has a high affinity to biomembranes and/or which is involved in the transport of the preproprotein through biomembranes. These transport processes are often accompanied by processing of the preproprotein into one of the mature forms of the protein.

Double-stranded nucleotide sequences will be shown as only one strand, for convenience.

BRIEF DESCRIPTION OF THE DRAWINGS

FIGS. 1-4 show amino acid and nucleotide sequences of various forms of preprothaumatin, prothaumatin, and prethaumatin.

FIG. 5 illustrates allelic variations in the preprothaumatin gene.

FIG. 6 shows some mutations introduced in the various allelic genes encoding preprothaumatin.

FIGS. 17-21 illustrate the construction of plasmids pUR 521-527, 531-537, and 541-547.

According to the invention a recombinant plasmid is provided comprising:

(i) structural genes coding for the various allelic forms of preprothaumatin or mutated forms of these structural genes (FIGS. 2, 3, 4, 5, 6).

Figure 7:
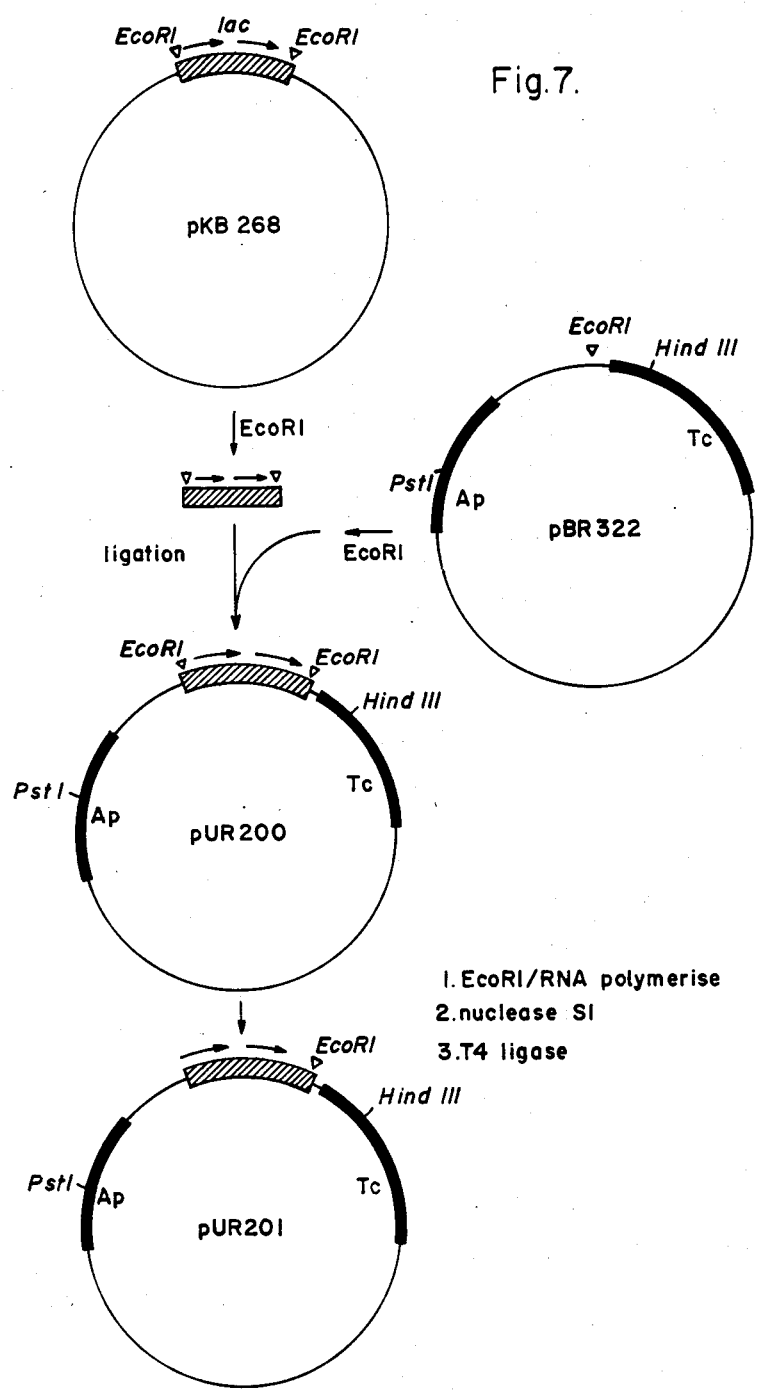
FIGS. 7-9 illustrate the construction of plasmids pUR201, pUR301, and pUR 401 respectively.

(ii) specific DNA sequences which regulate the expression of said structural genes. These specific DNA sequences consist of either an inducible or a constitutive regulon. A preferred inducible regulon consists of a double lac UV5 system as described by Goeddel et al., Nature 281, 544-548 (1979), plasmid pUR 201 (FIG. 7).

Another preferred inducible regulon is a constituent of the tryptophan system described by F. Lee et al., J. Mol. Biol. 121, 193-217 (1978) and K. Bertrand et al., Science 189, 22-26 (1975).

Figure 8:
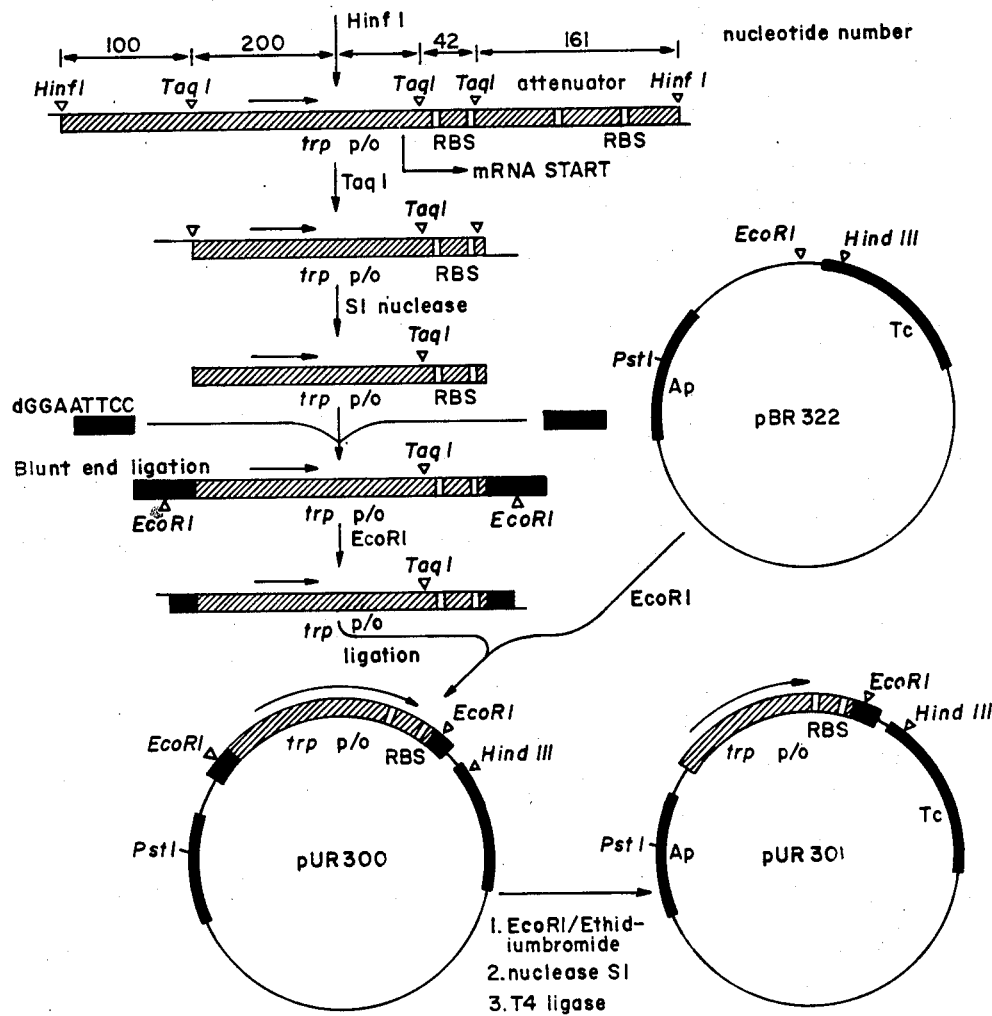

Applicants have modified this tryptophan system to obtain a more adequate system according to FIG. 8. In this modified system the attenuator region and the information for the 14-residue peptide in the leader transcript has been eliminated, while maintaining the ribosome binding site of the latter protein.

Figure 9:
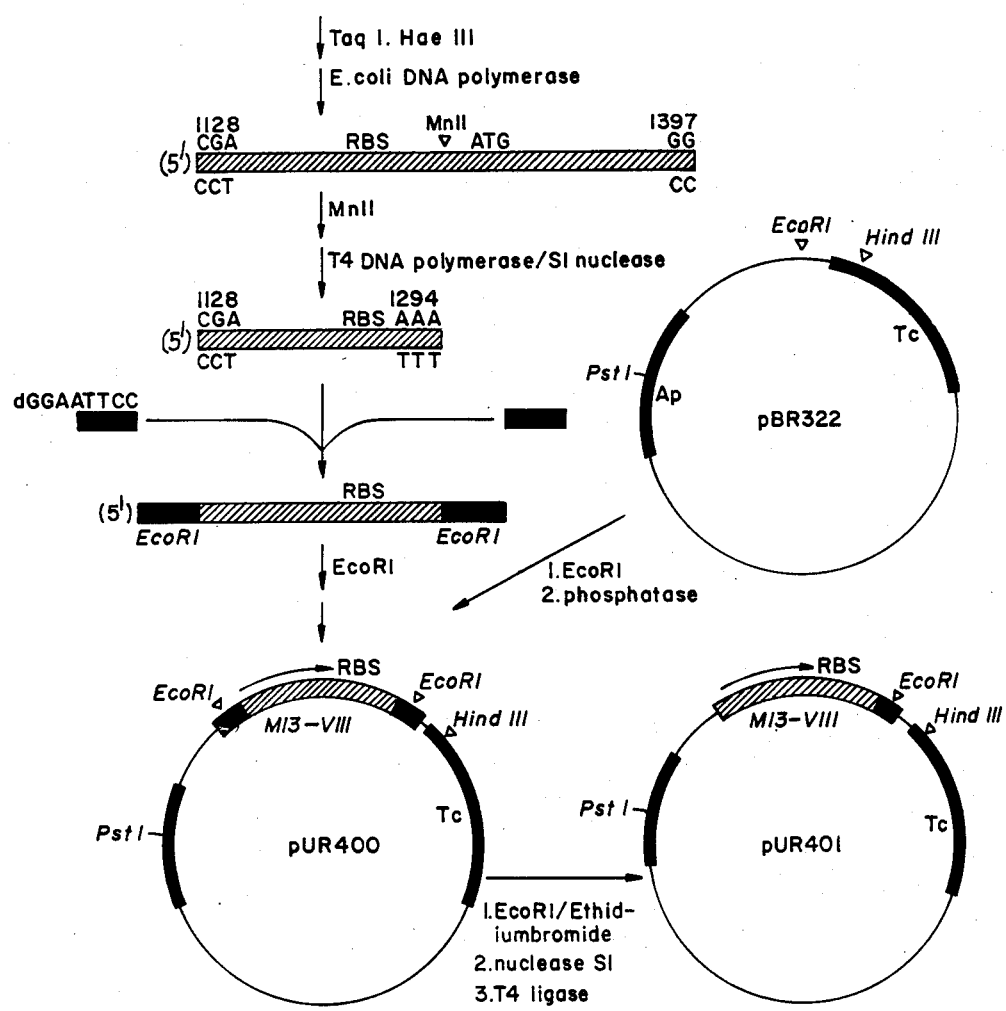

Also preferred are recombinant plasmids according to the invention which comprise DNA sequences consisting of a modified promoter/ribosome-binding site (FIG. 9) of gene VIII of bacteriophage M13, fd or fl, P. M. G. F. van Wezenbeek et al., Gene 11, 129-148 (1980), which, as far as Applicants are aware, were never used before for the expression of eukaryotic genes.

In the recombinant plasmid according to the invention the regulon may be either directly linked to the structural gene or indirectly through a novel start codon and EcoRI containing DNA linker comprising the nucleotide sequence (5')pCAT(N)$_n$GAATTC(N'-)$_n$ATG$_{OH}$(3') wherein n=0, 1, 2 or 3, and N and N' are any of the nucleotide A, T, G or C, with the proviso that in the double-stranded structure N and N' are such that a rotational symmetrical structure is present. By a rotational symmetrical structure is meant that were N is e.g. represented by A, N' should be represented by the complementary base T.

In some instances it turned out that the yield of expression improved when the sequence AATT between the regulon and the structural gene had been eliminated. The microbial cloning vehicles containing the natural or mutated structural genes encoding the various allelic forms of the preprothaumatin according to the invention are obtained and the various preprothaumatins are produced by performing a number of steps, the most essential of which are:

(1) isolation and purification of the messenger RNA (mRNA) of thaumatin;

(2) conversion of this mRNA into double-stranded DNA (ds DNA);

(3) construction of ds DNA having a poly-dC tail;

(4) incorporation of the ds DNA-poly-dC molecules in Pst I-cleaved and poly-dG-tailed plasmid pBR 322 DNA;

(5) transformation and clone selection;

(6) determination of the nature of the inserts by RNA/DNA hybridization and in vitro translation;

(7) double-checking the nature of the inserts by DNA- and RNA-sequence analysis;

(8a) producing DNA encoding the unprocessed preprothaumatin (FIGS. 1, 2 and 5);

(8b) producing DNA encoding prothaumatin (FIG. 3);

(8c) producing DNA encoding prethaumatin (FIG. 4);

(8d) producing DNA encoding the unprocessed preprothaumatin, except that special mutations have been introduced into the nucleotide sequence 32-97, particularly into the nucleotides 32-49 (FIGS. 1, 6);

(8e) producing DNA as described under (8a-8d), except that special mutations have been introduced into the nucleotide sequence 32-736, particularly into the nucleotide sequence 332-718 (FIGS. 1, 6);

(9) construction of plasmids comprising specific transcription regulating DNA-sequences, and chemical synthesis of DNA-linkers and -primers;

(10) construction of plasmids comprising a constitutive or inducible regulon and the ligated preprothaumatin genes as described under (8a-8e) and transformation of E. coli with said plasmids.

(11) culturing of E. coli cells containing said recombinant plasmids and detection and isolation of the preprothaumatins or their naturally processed forms.

The following detailed description will illustrate the invention.

1. Isolation and purification of mRNA (thaumatin)

Isolated arils of Thaumatococcus daniellii were ground under liquid nitrogen. After protein extraction with phenol, a selective precipitation of the RNAs with LiCl was performed following the procedure described by K. S. Kirby (1965), Biochem. J. 96, 226-269, U. Wiegers and H. Hilz (1972) FEBS Letters 23, 77-82.

Poly-A containing messenger RNA was recovered by several passages over oligo-dT-cellulose columns and from this messenger mixture the thaumatin-encoding mRNA, was isolated by polyacrylamide electrophoresis. This was checked by translation of the mRNA in the wheat germ system as described by H. Aviv and P.

Leder (1972) Proc. Natl. Acad. Sci., U.S.A, 69, 1408–1412, J. W. Davies and P. Kaesburg (1973), J. Virol. 12, 1434–1441.

2. Conversion of mRNA thaumatin into double-stranded DNA

The purified thaumatin mRNA was copied with AMV reverse transcriptase to yield a single-stranded DNA molecule, according to the procedure described by G. N. Buell et al., J. Biol. Chem. (1978) 253, 2471–2482. This DNA was subsequently converted into a double-stranded molecule by using *E. coli* DNA-polymerase, according to the procedure described by A. R. Davis et al., Gene 10, 205–218 (1980). The loop structure of the double-stranded DNA copy was removed by nuclease-S1-digestion.

3. Construction of double-stranded DNA with poly-dC tails

DNA-molecules of the desired length were obtained by polyacrylamide gel-electrophoresis, extracted from the gel an tailed with poly-dC by terminal transferase according to the procedure described by R. Roychoudhury et al., (1976) Nucleic Acids Research 3, 863–877.

4. Integration of the ds DNA-poly-dC molecules in the plasmid pBR 322

Plasmid pBR 322 was treated with the restriction endonuclease Pst I, that cleaves the plasmid at a recognition site that lies in the gene encoding the β-lactamase protein.

Subsequently pBR 322 was supplied with poly-dG tails by terminal transferase. The poly-dC DNA molecules were annealed to the poly-dG tailed plasmid pBR 322.

5. Transformation and clone selection

The plasmids thus obtained were transferred into CaCl$_2$-treated *E. coli* cells. After transformation cells containing hybrid plasmid DNA molecules were selected on their resistance to tetracycline. Positive colonies were screened for plasmids with large inserts by a combination of a rapid plasmid extraction procedure as outlined by H. C. Birnboim and J. Doly, Nucleic Acids Research 7, 1513–1523 (1979) and Pst I-digestion of the isolated DNA.

6. Determination of the nature of the inserts (I). Hybridization/in vitro translation From the selected clones 10 μg plasmid DNA were isolated, which subsequently were bound to diazotated (DBM) paper discs. The immobilized plasmid DNA molecules were then used in a hybridization/in vitro translation procedure as outlined by J. G. Williams et al., Cell 17, 903–913 (1979) in order to determine the nature of the DNA insert.

7. Determination of the nature inserts (II) by DNA- and RNA sequence analysis

The nucleotide sequence analysis of the thaumatin inserts was performed by the chemical degradation procedure as outlined by A. M. Maxam and W. Gilbert in Methods in Enzymology, L. Grossmann and K. Moldave editors, New York, Acad. Press, 1980, Vol. 65 (1), pages 499–560, and by the dideoxy/nick translation procedure as outlined by J. Maat and A. J. H. Smith, Nucleic Acids Research 5, 4537–4545 (1978).

Further information on the nucleotide sequence of the thaumatin mRNA was derived indirectly by primed synthesis by AMV-reverse transcriptase on the thaumatin mRNA template in the presence of chain terminating inhibitors, as outlined by D. Zimmern and P. Kaesberg, Proc. Natl. Acad. Sci., U.S.A. 75, 4257–4261 (1978). This screening yielded inter alia plasmid pUR 100 containing an almost complete copy of thaumatin mRNA.

8. Production of DNA encoding various maturation forms of preprothaumatin

8a. Production of DNA encoding for the unprocessed preprothaumatin

Plasmid pUR 100 was treated with the restriction endonuclease Pst I and the DNA sequence containing at least the nucleotides 31–793 (FIG. 1) was subsequently treated with restriction endonuclease Hae III generating inter alia a DNA fragment running from position 36–143. This fragment was blunt-end ligated with the chemically synthesized linker (5')pCCGGATCC-GG$_{OH}$(3'), then treated with the restriction endonuclease Bam HI, subsequently ligated in the restriction endonuclease Bam HI site of pBR 322 and cloned in *E. coli*. Plasmid DNA containing the cloned fragment was treated with Hpa II and S1 nuclease, resulting in the nucleotide sequence

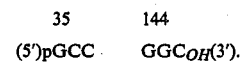

This sequence was blunt end ligated to the chemically synthesized linker (5')pCAT(N)$_n$GAATTC(N')$_n$AT-G$_{OH}$(3'), treated with restriction endonuclease EcoRI, subsequently integrated in the EcoRI site of pBR 322 and cloned in *E. coli*.

Figure 10:
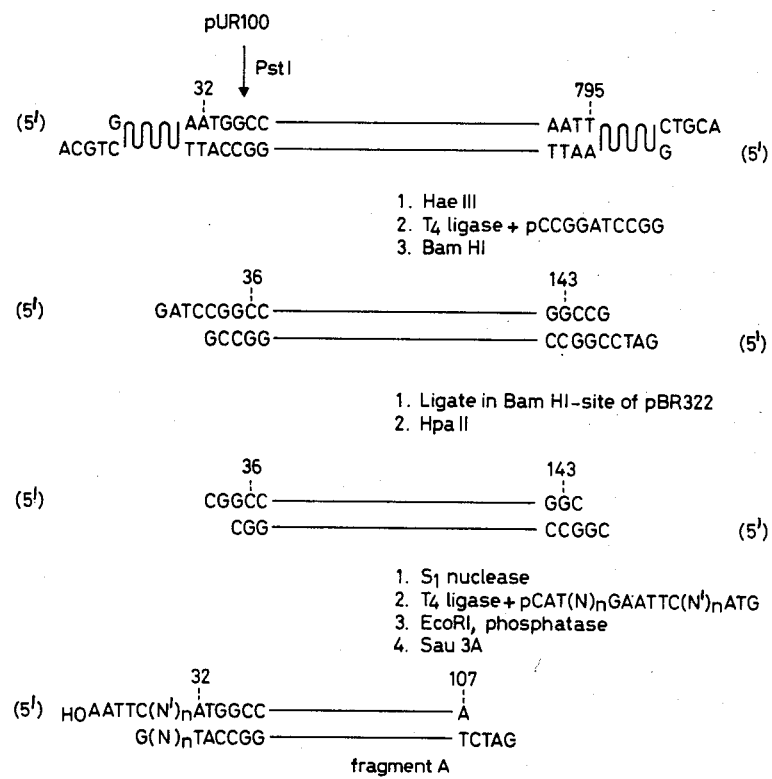
FIG. 10 shows the construction of the preprothaumatin gene without G/C-tails.

The plasmids with the preprothaumatin insert were treated with EcoRI and restriction endonuclease Sau 3A, resulting in fragment A of FIG. 10.

Figure 11:
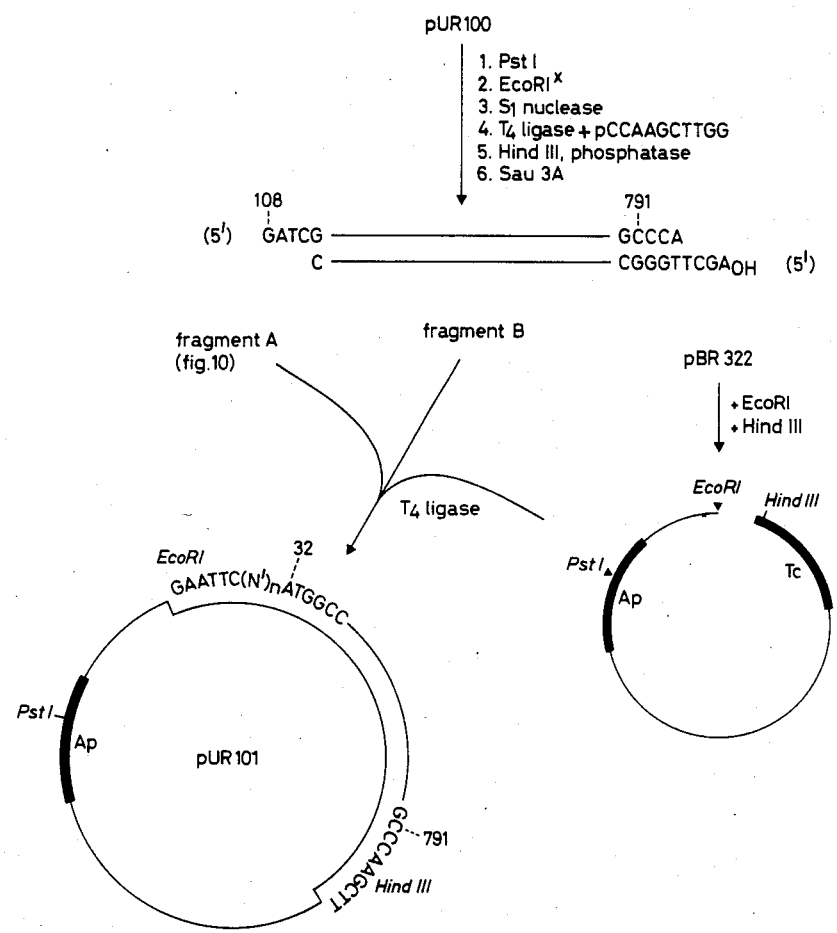
FIGS. 11-14 illustrate the construction of pUR101, M13-101-A, and M13-101-B, pUR102, and pUR103 respectively.

Plasmid pUR 100 was treated with restriction endonuclease Pst I and with EcoRI in the presence of Mn++ (1 mmol/l). Under this condition EcoRI recognize the sequence AATT. After S1 nuclease treatment this DNA fragment was blunt-end ligated with the chemically synthesized linker (5')pCCAAGCTT-GG$_{OH}$(3') and subsequently treated with restriction endonucleases Hind III and Sau 3A resulting in fragment B (with Sau 3A site at nucleotide position 109 and a Hind III site after position 791). The fragments A and B were ligated and subsequently integrated into the EcoRI and Hind III treated pBR 322, resulting in plasmid pUR 101 (FIG. 11).

A single-stranded DNA template was obtained by cloning the EcoRI-Hind III fragment of pUR 101, after repair synthesis with Klenow-DNA polymerase and addition of EcoRI-linker (5')pGGAATTCC$_{OH}$(3') in the EcoRI site of RF M13-mp2.

Figure 12:
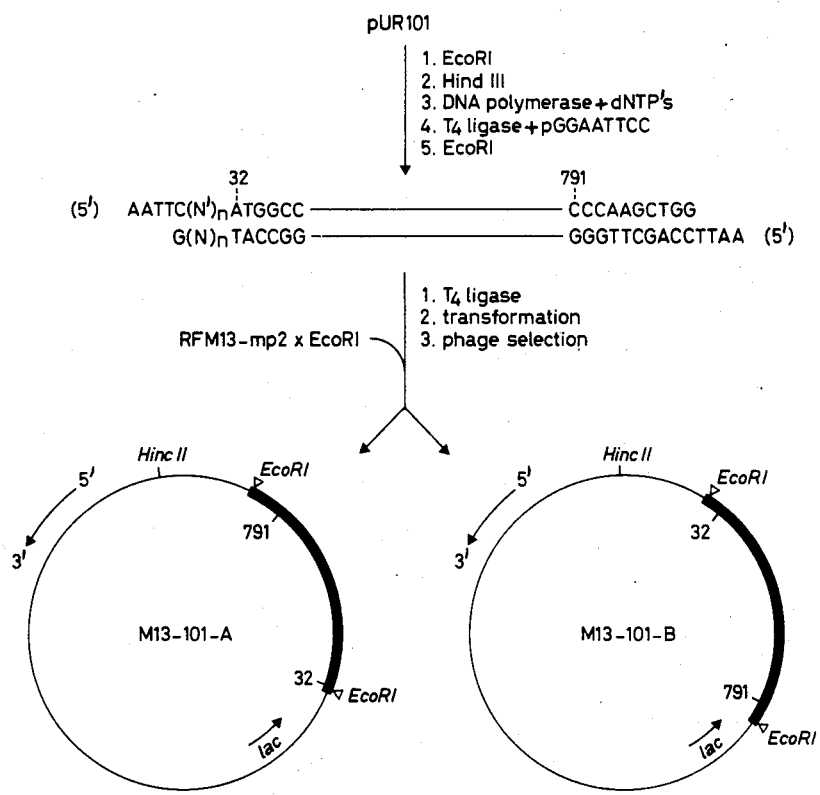

Clone M13-101-A has the preprothaumatin DNA inserted such that the single strand has the same polarity as the thaumatin mRNA; clone M13-101-B has the preprothaumatin DNA inserted such that the single strand has the opposite polarity as the thaumatin mRNA (FIG. 12).

8b. Production of DNA encoding prethaumatin

The single-stranded DNA of M13-101-A was used as a template for complementary DNA synthesis, using the chemically synthesized DNA sequence (5')pTCAGGCAGTAGGGC$_{OH}$(3') as a primer. After heat denaturation of the ds DNA, the complementary DNA strand served as a template for DNA synthesis using the fragment.

Figure 13:
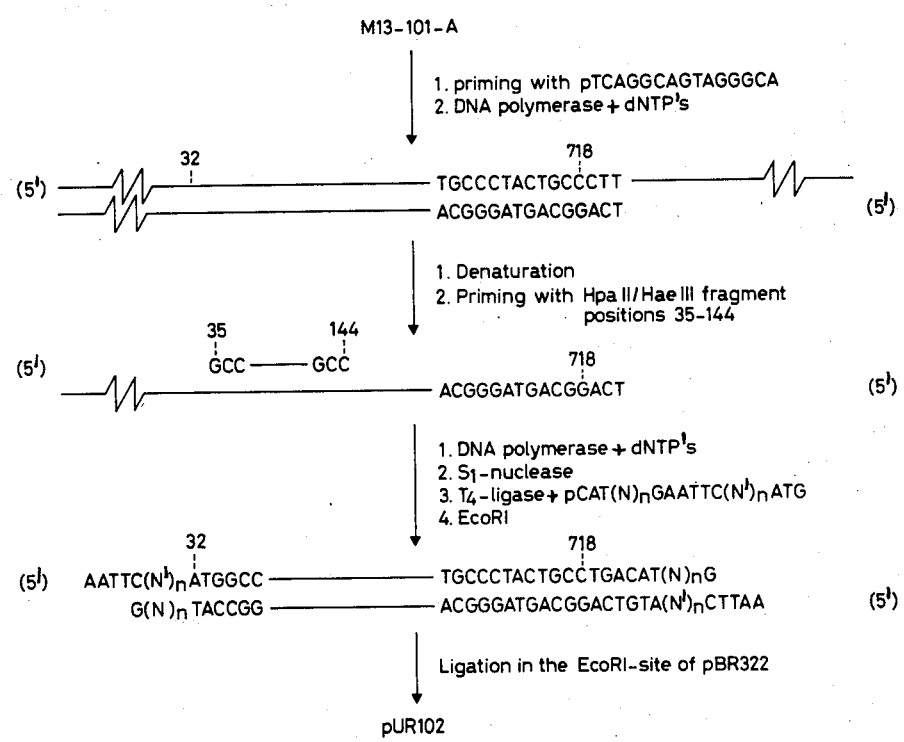

35            144
    (5')pGCC    GGC$_{OH}$(3'), whose synthesis is described under 8a, as a primer. Subsequently, the obtained ds DNA fragment was treated with S1-nuclease and blunt end ligated with the EcoRI-linker (5')pCAT(N)$_n$GAATTC(N')$_n$ATG$_{OH}$(3') (FIG. 13). This DNA was digested with EcoRI and integrated in the EcoRI restriction site of pBR 322 resulting in plasmid pUR 102, containing the prethaumatin nucleotide sequence 32-718.

8c. Production of DNA encoding prothaumatin

The single-stranded DNA of M13-101-B was used as a template for complementary DNA synthesis, using the chemically synthesized DNA sequence (5')pGCCACCTTCG$_{OH}$(3') as a primer. The formed ds DNA was treated with EcoRI and S1 nuclease and subsequently blunt end ligated with the chemically synthesized EcoRI linker (5')pCAT(N)$_n$GAATTC(N'-)$_n$ATG$_{OH}$(3').

Figure 14:
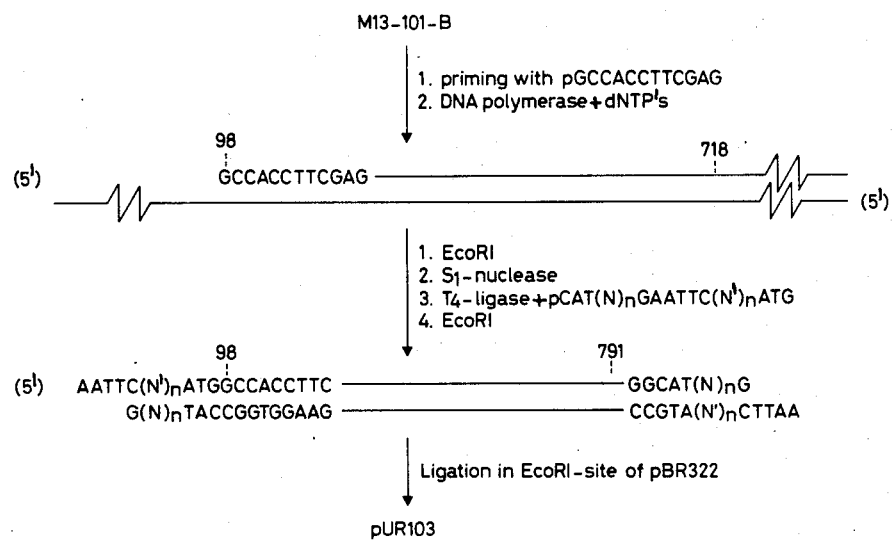

This fragment was treated with EcoRI and then integrated in the EcoRI restriction site of pBR 322, resulting in the plasmid pUR 103, containing the prothaumatin nucleotide sequence 98-736 (FIG. 14).

8d. Production of DNA encoding the unprocessed preprothaumatin, except that special mutations have been introduced into the nucleotide sequence 32-97, particularly into the nucleotides 32-49.

Figure 15:
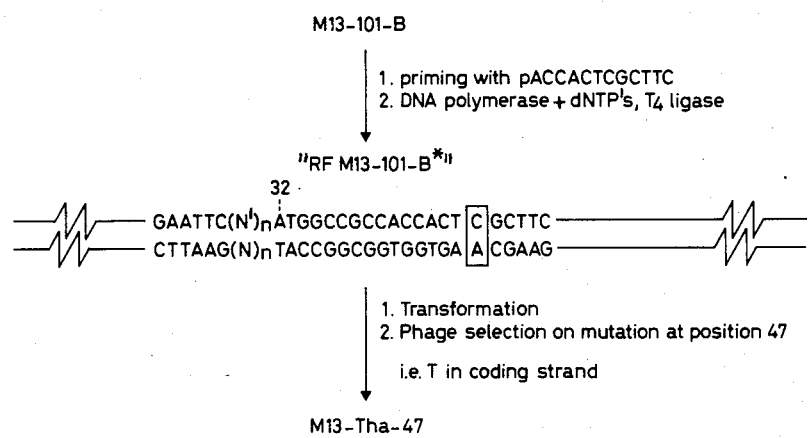
FIG. 15 shows the construction of M13-Tha47.

The single-stranded DNA of M13-101-B was used as a template for complementary DNA synthesis using the chemically synthesized DNA sequence (5')pACCACTCGCTTC$_{OH}$(3') as a primer. After transformation of E. coli with the ds DNA, the phage DNA with the mutation (T replaced by C at position 47) was selected by DNA sequence analysis. These phages were coded M13 Tha 47 (FIG. 15).

8e. Production of DNA coding for any of the sequences described under (8a-8d), except that special mutations have been introduced into the nucleotide sequence 32-736, particularly into the nucleotide sequence 332-718.

Figure 16:
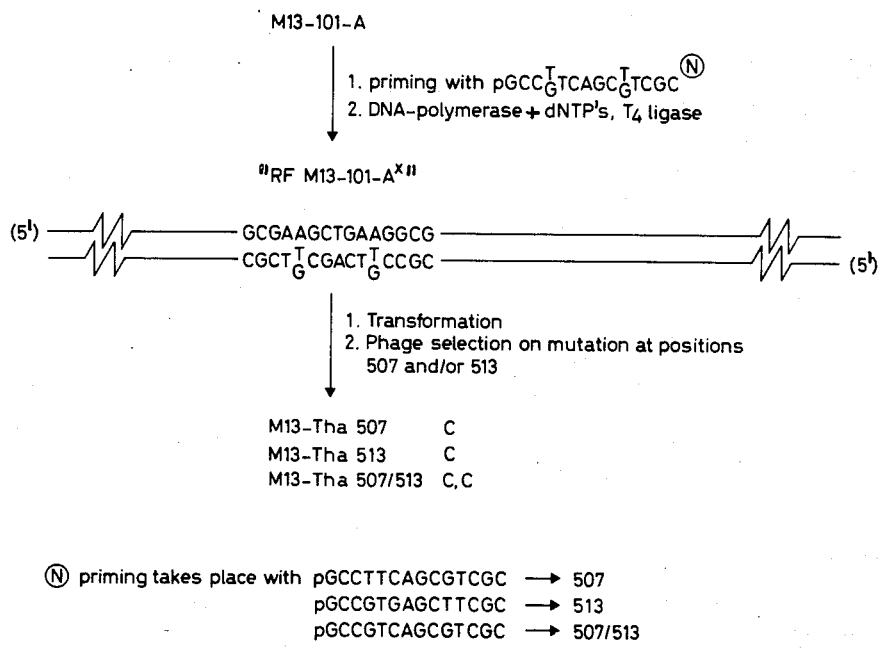
FIG. 16 shows the construction of M13-Tha507, M13-Tha513, and M13-Tha507/513.

The single-stranded DNA of M13-101-A was used as a template for DNA synthesis using the Klenow DNA-polymerase and the chemically synthesized primers (5')pGCCTTCAGCGTCGC$_{OH}$(3'), (5')pGCCGTCAGCTTCGC$_{OH}$(3') and (5')pGCCGTCAGCGTCGC$_{OH}$(3'). All these sequences are complementary to the nucleotides 503-516 of the preprothaumatin gene (FIG. 4) with one or two modifications to introduce the desired change in the protein. After transformation of E. coli with the ds DNAs, the phages with the modifications aimed at were selected by DNA sequence analysis. These pages were coded M13 Tha 507, 513, 507/513 (FIG. 16).

9a. Construction of a plasmid pUR 201

A fragment containing 285 base pairs comprising the double lac regulon (lac UV5) was obtained by restriction endonuclease EcoRI cleavage of pKB 268, (K. Backman and M. Ptashne, Cell 13, 65-71 (1978)). This fragment was ligated in the EcoRI site of pBR 322 DNA. Plasmid DNA with the lac regulon in the right orientation (FIG. 7.) was partly cleaved by EcoRI in the presence of E. coli RNA polymerase. The EcoRI cleavage site most distant from the restriction endonuclease Hind III cleavage site was preferentially attacked. The linearized DNA was treated with S1 nuclease, purified by agarose gel electrophoresis, circularized by ligation with T4 DNA-ligase and subsequently used to transform E. coli. From the tetracycline-resistant transformants pUR 201 with the correct structure (FIG. 7) was obtained.

9b. Construction of plasmid pUR 301

A DNA fragment of about 510 base pairs was obtained by restriction endonuclease Hinf I cleavage of ptrp ED5 (R. A. Hallewell and S. Emtage, Gene 9, 27-47 (1980)). This fragment was cleaved with restriction endonuclease Taq I in the presence of E. coli RNA polymerase. The Taq I site in the trp regulon (described by K. Bertrand et al., Science 189, 22-26 (1975) and F. Lee et al., J. Mol. Biol. 121, 193-217 (1978)) was selectively protected, thus yielding a fragment containing 234 base pairs comprising the trp regulon (FIG. 8). This fragment was then treated with S1 nuclease, blunt-end ligated with the EcoRI-linker (5')pGGAATTCC$_{OH}$(3'), cut with EcoRI and subsequently cloned in the EcoRI-site of pBR 322.

Plasmid pUR 300 with the trp regulon in the correct orientation (FIG. 8) was isolated. The EcoRI-cleavage site most distant from the Hind III site was removed by partial cleavage of pUR 300 DNA by EcoRI in the presence of ethidium bromide and S1 nuclease treatment. Linear DNA molecules were recirculated by T4 DNA ligase. From the tetracycline-resistant transformants pUR 301 with the structure as outlined in FIG. 8 was obtained.

9c. Construction of Plasmid pUR 401

A fragment containing 269 base pairs (DNA sequence 1128-1379) was obtained by digestion of RF M13 DNA (see P. M. G. F. v. Wezenbeek et al., Gene 11, 129-148 (1980)), with the restriction endonucleases Taq I and Hae III and the Taq I site was made blunt-ended by a repair reaction with E. coli DNA polymerase; the fragment was subsequently partly digested with restriction enzyme Mnl I. The partial products were treated with successive actions of T4 DNA polymerase and S1 nuclease and subsequently blunt-end ligated with the EcoRI-linker (5')pGGAATTCC$_{OH}$(3'), then treated with EcoRI and ligated in the EcoRI site of the pBR 322. By restriction enzyme analysis and DNA sequence analysis a plasmid was obtained in which the EcoRI cleavage site was located just beyond the ribosome-binding site of the M13 gene VIII DNA sequence. Applicants have found that the plasmids having the M13 regulon from nucleotide 1128 to nucleotide 1291 to 1297 were appropriate regulons for expression. The EcoRI cleavage site most distant from the Hind III site was removed essentially as described for pUR 301. The complete construction of pUR 401 is outlined in FIG. 9.

9d. Chemical synthesis of linkers and primers

The synthesis were carried out with the phosphotriester method described by J. F. M. de Rooy et al., Recl. Trav. Chim. Pays Bas, 98, 537-548 (1979).

10. Construction of expression plasmids comprising a constitutive or an inducible regulon and the ligated preprothaumatin genes described under (8a-8e) and transformation of E. coli with said plasmids.

Figure 17:
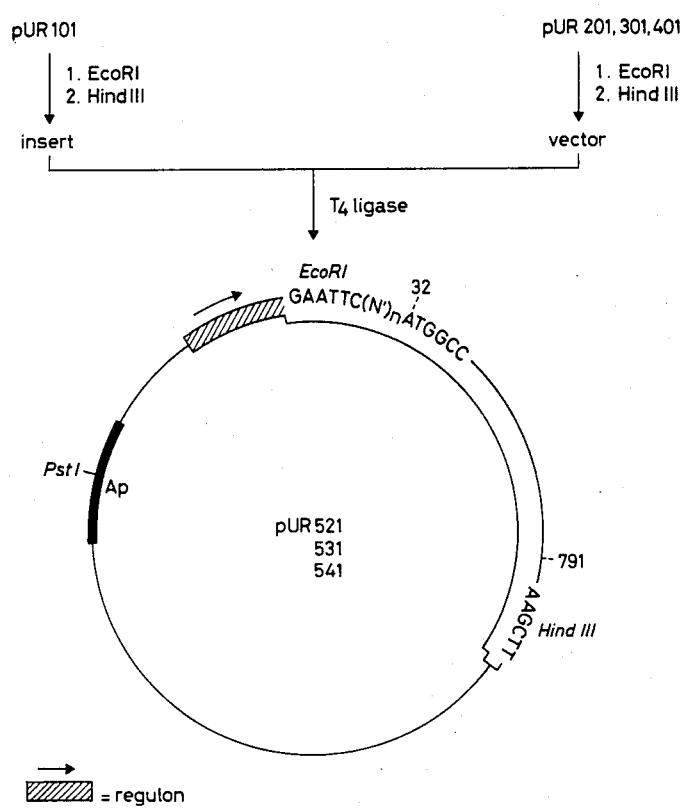

10a. The preprothaumatin encoding DNA fragment of plasmid pUR 101 was obtained by treatment of pUR 101 with the restriction endonucleases EcoRI and Hind III. Subsequently this DNA fragment was integrated in the EcoRI and Hind III site or the plasmids pUR 201 of pUR 301 or pUR 401, resulting in the expression plasmids pUR 521, pUR 531 and pUR 541 respectively (FIG. 17).

Figure 18:
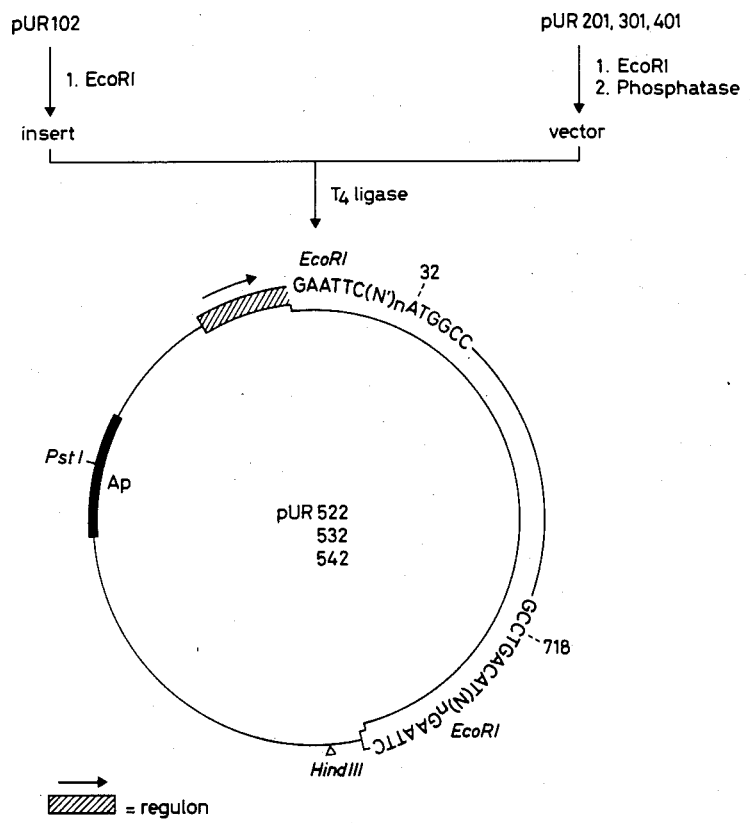

10b. The prethaumatin encoding DNA fragment of plasmid pUR 102 was obtained by treatment of pUR 102 with the restriction endonuclease EcoRI and subsequently integrated in the EcoRI site of the plasmids pUR 201 or pUR 301 or pUR 401, resulting in the expression plasmids pUR 522, pUR 532 and pUR 542 respectively (FIG. 18).

Figure 19:
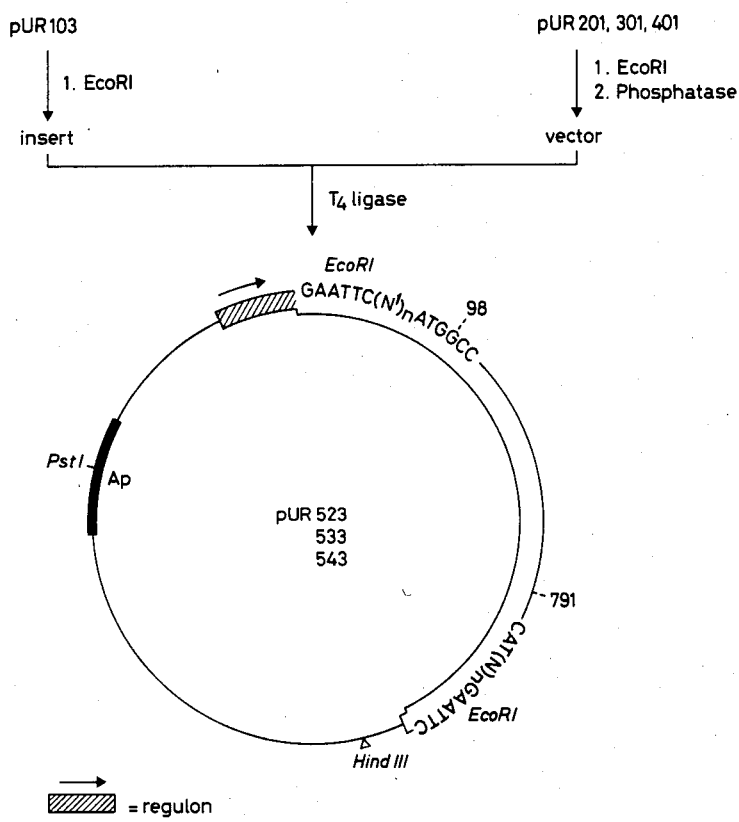

10c. The prothaumatin encoding DNA fragment of plasmid pUR 103 was obtained by treatment of pUR 103 with the restriction endonuclease EcoRI and subsequently integrated in the EcoRI site of plasmids pUR 201 or pUR 301 or pUR 401, resulting in the expression plasmids pUR 523, pUR 533 and pUR 543 (FIG. 19).

10d. RF M13 Tha 47 DNA was treated with EcoRI and the DNA fragment encoding preprothaumatin was subsequently integrated in the EcoRI site of plasmids pUR 201 or pUR 301 or pUR 401, resulting in the expression plasmids pUR 524, pUR 534 and pUR 544 respectively (FIG. 20).

10e. RF M13 Tha 507 or RF M13 Tha 513 or RF M13 Tha 507/513 DNA was treated with EcoRI and the DNA fragments encoding the mutated forms of preprothaumatin were subsequently integrated in the EcoRI site of plasmids pUR 201 or pUR 301 or pUR 401, resulting in the double lac expression plasmids pUR 525–527 (containing preprothaumatin mutated at positions 507, 513 and 507 and 513 respectively), the trp expression plasmids pUR 535–537 (containing preprothaumatin mutated at positions 507, 513 and 507 and 513 respectively) and the M13 expression plasmids pUR 545–547 (containing preprothaumatin mutated at positions 507, 513 and 507 and 513 respectively) (FIG. 21).

In all the plasmids described under (10a–10e) the AATT sequence originating from the chemically sythesized linkers could be deleted by cleavage of the plasmids with EcoRI in the presence of ethidium bromide; linear partials were isolated by agarose gel electrophoresis, treated with S1 nuclease and recircularized by T4 ligase. Plasmids with an AATT deletion were isolated by restriction enzyme analysis and the deletion was confirmed by DNA sequence analysis.

11. Culturing of *E. coli* cells containing said plasmids and detection of preprothaumatin and its various maturation forms.

*E. coli* cells containing one of the plasmids pUR 521–527, pUR 531–537 and pUR 541–547 with or without the AATT sequence in the linker between the regulon and the preprothaumatin genes in the correct orientation and reading frame were cultured under optimal conditions for their growth—these culturing conditions vary with the type of plasmid present in the cells—but a suitable antibiotic was always present to maintain selection pressure.

Under these conditions the cells containing either plasmids pUR 521–527 or pUR 531–537 or pUR 541–547 produced considerable amounts of various forms of preprothaumatin.

The presence of the protein was demonstrated qualitatively by SDS gel electrophoresis of cell extracts from which preprothaumatin or its maturation forms were isolated by specific immunoprecipitation, by physiological tests on their sweetness and by a specially developed enzyme-linked immunosorbent assay (Elisa). The antisera for this test were generated by injecting the thaumatin produced by the plant *Thaumatococcus daniellii*, supplemented with Freund adjuvant in sheep as wel as in rabbits.

"Cells of *E. coli* strains K12(294) containing plasmids pUR 531, pUR 522 or pUR 523 were deposited under the Budapest Treaty on Dec. 2, 1981, at the American Type Culture Collection, 12301 Parklawn Drive, Rockville, Md., U.S.A. and have acquired the following registration numbers: ATCC 39015, ATCC 39016 and ATCC 39017, respectively."

We claim:

1. A recombinant DNA sequence comprising DNA sequence selected from the group consisting of
   (i) the preprothaumatin gene, of the sequence

```
      32                          47
       |                           |
ATG GCC GCC ACC ACT QGC TTC TTC TTC

71
                           |
CTC TTC CCC TTC CTC CTC CTC CTC ACG 92      98                  110
           |       |                    |
CTC TCC CGC GCT GCC ACC TTC GAG ATC

GTC AAC CGC TGC TCC TAC ACC GTG TGG 149  152
                  |    |
GCG GCC GCC TCC AAA GGC GAC GCC GCC

188
                                   |
CTG GAC GCC GGC GGC CGC CAG CTC AAC

212
                               |
TCG GGA GAG TCC TGG ACC ATC AAC GTA 227       235
         |         |
GAA CCC GGC ACC AAR GGT GGC AAA ATC 266       272
                               |         |
TGG GCC CGC ACC GAC TGC TAT TTC GAC 284                296   297
                   |                   |    /
GAC AGC GGC SGC GGC ATC TGC UVG ACC 305                          324
      |                            |
GGC GAC TGC GGC GGC CTC CTC CWG TGC 332              344
      |                |
AAG CGC TTC GGC CGG CCG CCC ACC ACG

CTG GCG GAG TTC TCG CTC AAC CAG TAC 383              392
 |                |
GGC AAG GAC TAC ATC GAC ATC TCC AAC 422            434
                       |              |
ATC AAA GGC TTC AAC GTG CCG ATG XAC 452        461
                           |          |
TTC AGC CCG ACC ACG CGC GGC TGC CGC

GGG GTG CGG TGC GCC GCC GAC ATC GTG 500       507   512   513
             |         |     |    /
GGG CAG TGC CCG GCG AYG CTG AZG GCG

539
                                 |
CCG GGG GGT GGT TGC AAC GAT GCG TGC

ACC GTG TTC CAG ACG AGC GAG TAC TGC
```

-continued

```
572        578
 |          |
TGC ACC ACG GGG AAG TGC GGG CCG ACG

617
                           |
GAG TAC TCG CGC TTC TTC AAG AGG CTT

632
             |
TGC CCG GAC GCG TTC AGT TAT GTC CTG

656
  |
GAC AAG CCA ACC ACC GTC ACC TGC CCC 692 695
             |   |
GGC AGC TCC AAC TAC AGG GTC ACT TTC

718
                 |
        TGC CCT ACT GCC CTT GAA 734  736
                         |   /
            CTT GAA GAC GAG     ,
``` wherein Q (47)=T, R (235)=G, S (284)=C, U (296)=C, V (297)=G, W (324)=A, X (434)=G, Y (507)=A, and Z (513)=A;

(ii) the prothaumatin coding sequence consisting of the sequence from positions 98–736 inclusive as recited in (i) above;

(iii) the prethaumatin coding sequence consisting of the sequence from positions 32–718 inclusive as recited in (i) above;

(iv) the preprothaumatin allelic form coding sequence consisting of the sequence from positions 32–736 inclusive as recited in (i) above and except wherein R=C;

(v) the preprothaumatin allelic form coding sequence consisting of the sequence from positions 32–736 inclusive as recited in (i) above and except wherein S=A;

(vi) the preprothaumatin allelic form coding sequence consisting of the sequence from positions 32–736 inclusive as recited in (i) above and except wherein U=A and V=A;

(vii) the preprothaumatin allelic form coding sequence consisting of the sequence from positions 32–736 inclusive as recited in (i) above and except wherein W=G;

(viii) the preprothaumatin allelic form coding sequence consisting of the sequence from positions 32–736 inclusive as recited in (i) above and except wherein X=A;

(ix) the mutated preprothaumatin allelic form coding sequence consisting of the sequence from positions 32–736 inclusive as recited in (i) above and except wherein Q=C;

(x) the mutated preprothaumatin allelic form coding sequence consisting of the sequence from positions 32–736 inclusive as recited in (i) above and except wherein Y=C; and (xi) the mutated preprothaumatin allelic form coding sequence consisting of the sequence from positions 32–736 inclusive as recited in (i) above and except wherein Z=C.

2. Recombinant plasmids comprising
   (i) a DNA sequence as claimed in claim 1, and
   (ii) an inducible or constitutive promoter and operator region wherein said region regulates the expression of said DNA sequence.

3. A bacterial culture comprising *E. coli* cells containing any one of the recombinant plasmids as claimed in claim 2.

4. A process for producing preprothaumatin, prethaumatin or prothaumatin by incorporating the recombinant plasmids as claimed in claim 2 in *E. coli* cells, culturing the transformed cells and isolating the protein produced by said cells.

5. Recombinant plasmids comprising:
   (i) a DNA sequence as claimed in claim 1; and
   (ii) an inducible promoter and operator region consisting of a double lac UV5 system regulating the expression of said DNA sequence.

6. Recombinant plasmids comprising:
   (i) a DNA sequence as claimed in claim 1; and
   (ii) a modified tryptophan system regulating the expression of said DNA sequence, said system consisting essentially of the trp promoter/operator region extending just beyond the ribosome binding site of the DNA sequence encoding the trp leader peptide.

* * * * *

UNITED STATES PATENT AND TRADEMARK OFFICE
CERTIFICATE OF CORRECTION

PATENT NO. : 4,771,000

DATED : September 13, 1988

INVENTOR(S) : VERRIPS ET AL.

It is certified that error appears in the above-identified patent and that said Letters Patent is hereby corrected as shown below:

On the title page:

Item [73] change, Assignee from "Internationale Octrooi Maatschappij Octropa B.V., Rotterdam, Netherlands" to --Unilever Patent Holdings B.V., Rotterdam, Netherlands--

Column 1, lines 13 and 14, delete "consisting".

Column 2, line 49, change "(FIG. 4)" to --(FIG. 2)--.

Column 4, line 61, chnage "226" to --266--.

Column 5, line 20, change "an" to --and--.

Column 6, line 38, change "recognize" to to --recognizes--.

Column 8, line 65, change "of" to --or--.

Signed and Sealed this

Fifth Day of January, 1993

Attest:

DOUGLAS B. COMER

Attesting Officer

Acting Commissioner of Patents and Trademarks